(12) United States Patent
i Blasco et al.

(10) Patent No.: US 7,038,047 B2
(45) Date of Patent: May 2, 2006

(54) SUBSTITUTED 6-(2-METHOXYPHENYL) TRIAZOLOPYRIMIDES AS FUNGICIDES

(75) Inventors: Jordi Tormo i Blasco, Limburgerhof (DE); Hubert Sauter, Mannheim (DE); Bernd Müller, Frankenthal (DE); Markus Gewehr, Kastellaun (DE); Wassilios Grammenos, Ludwigshafen (DE); Thomas Grote, Wachenheim (DE); Andreas Gypser, Mannheim (DE); Joachim Rheinheimer, Ludwigshafen (DE); Ingo Rose, Mannheim (DE); Peter Schäfer, Ottersheim (DE); Frank Schieweck, Hessheim (DE); Michael Rack, Heidelberg (DE); Eberhard Ammermann, Heppenheim (DE); Siegfried Strathmann, Limburgerhof (DE); Gisela Lorenz, Hambach (DE); Reinhard Stierl, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 204 days.

(21) Appl. No.: 10/483,599

(22) PCT Filed: Jul. 8, 2002

(86) PCT No.: PCT/EP02/07577

§ 371 (c)(1),
(2), (4) Date: Jan. 12, 2004

(87) PCT Pub. No.: WO03/008416

PCT Pub. Date: Jan. 30, 2003

(65) Prior Publication Data

US 2004/0167136 A1   Aug. 26, 2004

(30) Foreign Application Priority Data

Jul. 18, 2001   (EP) .................... 01117406

(51) Int. Cl.
C07D 487/04   (2006.01)
C07C 69/612   (2006.01)
A01N 43/90   (2006.01)

(52) U.S. Cl. .................... 544/263; 514/259.31; 560/82

(58) Field of Classification Search ........... 514/259.31; 544/263; 560/82
See application file for complete search history.

(56) References Cited

U.S. PATENT DOCUMENTS

| 4,567,262 A | 1/1986 | Grimmer et al. |
| 4,567,263 A | 1/1986 | Eicken et al. |

FOREIGN PATENT DOCUMENTS

| EP | 550 113 | 7/1993 |
| EP | 770 615 | 5/1997 |
| EP | 945 453 | 9/1999 |
| EP | 1 002788 | 5/2000 |
| FR | 2 765875 | 1/1999 |
| WO | 98/46607 | 10/1998 |
| WO | 98/46608 | 10/1998 |
| WO | 99/48893 | 9/1999 |

OTHER PUBLICATIONS

Chemistry Letters, pp. 267-370, 1981.

*Primary Examiner*—Thomas C. McKenzie
(74) *Attorney, Agent, or Firm*—Novak Druce & Quigg LLP; Jason D. Voight

(57) ABSTRACT

Substituted 6-(2-methoxy-phenyl)-triazolopyrimidines of formula I

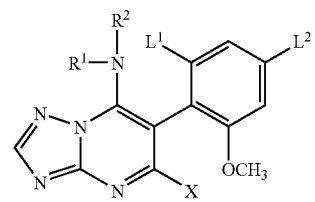

in which
$R^1$ and $R^2$ independently denote hydrogen or alkyl, alkenyl, alkynyl, or alkadienyl, haloalkyl, haloalkenyl, cycloalkyl, phenyl, naphthyl, or 5- or 6-membered heterocyclyl, containing one to four nitrogen atoms or one to three nitrogen atoms and one sulfur or oxygen atom, or 5- or 6-membered heteroaryl, containing one to four nitrogen atoms or one to three nitrogen atoms and one sulfur or oxygen atom, or
where $R^1$ and $R^2$ radicals may be unsubstituted or substituted as defined in the description, or
$R^1$ and $R^2$ together with the interjacent nitrogen atom represent a 5- or 6-membered heterocyclic ring, containing one to four nitrogen atoms or one to three nitrogen atoms and one sulfur or oxygen atom, which may be substituted;
$L^1$, $L^2$ independently denote hydrogen or halogen, provided that at least one from $L^1$ or $L^2$ is halogen;
X is halogen, cyano, alkyl, alkoxy, haloalkoxy or alkenyloxy;

processes for their preparation, compositions containing them and to their use for combating phytopathogenic fungi.

9 Claims, No Drawings

SUBSTITUTED 6-(2-METHOXYPHENYL) TRIAZOLOPYRIMIDES AS FUNGICIDES

The invention relates to substituted 6-(2-methoxy-phenyl)-triazolopyrimidines of formula I

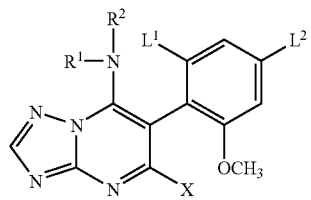

I in which
  $R^1$ and $R^2$ independently denote hydrogen or $C_1$–$C_{10}$-alkyl, $C_2$–$C_{10}$-alkenyl, $C_2$–$C_{10}$-alkynyl, or $C_4$–$C_{10}$-alkadienyl, $C_1$–$C_{10}$-haloalkyl, $C_2$–$C_{10}$-haloalkenyl, $C_3$–$C_{10}$-cycloalkyl, phenyl, naphthyl, or
  5- or 6-membered heterocyclyl, containing one to four nitrogen atoms or one to three nitrogen atoms and one sulfur or oxygen atom, or 5- or 6-membered heteroaryl, containing one to four nitrogen atoms or one to three nitrogen atoms and one sulfur or oxygen atom, or
  where $R^1$ and $R^2$ radicals may be unsubstituted or partly or fully halogenated or may carry one to three groups $R^a$,
  $R^a$ is cyano, nitro, hydroxyl, $C_1$–$C_6$-alkyl, $C_3$–$C_6$-cycloalkyl, $C_1$–$C_6$-alkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkynyl, $C_3$–$C_6$-alkynyloxy and $C_1$–$C_4$-alkylenedioxy; or
  $R^1$ and $R^2$ together with the interjacent nitrogen atom represent a 5- or 6-membered heterocyclic ring, containing one to four nitrogen atoms or one to three nitrogen atoms and one sulfur or oxygen atom, which may be substituted by one to three $R^a$ radicals;
  $L^1$, $L^2$ independently denote hydrogen or halogen, provided that at least one from $L^1$ or $L^2$ is halogen;
  X is halogen, cyano, $C_1$–$C_6$-alkyl, $C_1$–$C_6$-alkoxy, $C_1$–$C_6$-haloalkoxy or $C_3$–$C_8$-alkenyloxy.

Moreover, the invention relates to processes for their preparation, compositions containing them and to their use for combating phytopathogenic fungi.

6-Phenyl-7-amino-triazolopyrimidines are generally known from U.S. Pat. No. 4,567,262.

Triazolopyrimidines with a trifluorophenyl group in 6-position are disclosed in WO-A 98/46607 and EP-A 945 453.

From WO-A 98/46608 diverse 6-phenyl-triazolopyrimidines are known, which are substituted in the 7-position by fluorinated alkylamines.

From EP-A 550 113 triazolopyrimidines with a 2-methoxy substituted 6-phenyl group are known.

The compounds disclosed in the documents discussed above are said to be active against various phytopathogenic fungi.

It is an object of the present invention to provide compounds having improved fungicidal activity.

We have found that this object is achieved by the compounds defined at the outset. Furthermore, we have found processes for their preparation, compositions comprising them and methods for controlling phytopathogenic fungi using the compounds I.

The compounds of formula I differ from the compounds known from closest prior art EP-A 550 113 in the 2-methoxy-phenyl group, which is further halogenated.

Compounds of formula I can be prepared similar to the conditions known from EP-A 550 113. Preferably the preparation of compounds of formula I as defined above comprises reacting 5-amino-triazole with 2-(2-methoxy-phenyl)-substituted malonic acid ester of formula II, in which

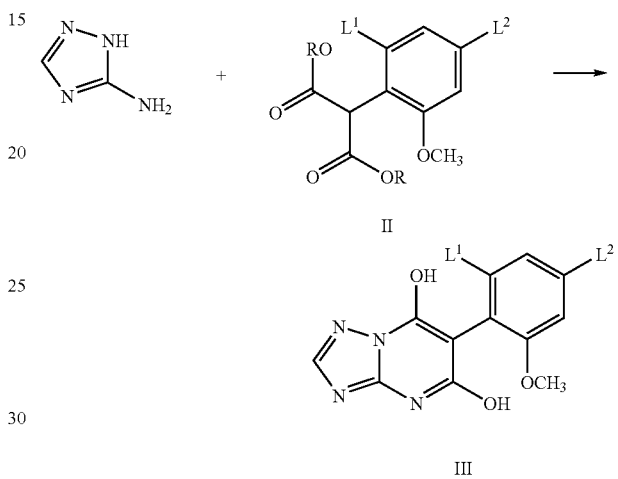

R represents alkyl, preferably $C_1$–$C_6$-alkyl, in particular methyl or ethyl, under alkaline conditions, preferably using high boiling tertiary amines as for example tri-n-butylamine as disclosed for example by EP-A 770 615 to yield compounds of formula III.

The resulting 5,7-dihydroxy-6-phenyl-triazolopyrimidine of formula III, wherein $L^1$ and $L^2$ are as defined for formula I, is subsequently treated with a halogenating agent, preferably with a brominating or chlorinating agent, such as phosphorus oxybromide or phosphorus oxychloride, neat or in the presence of a solvent to give IV.

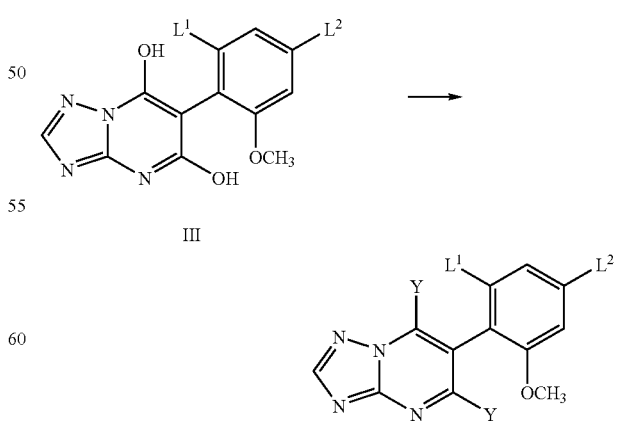

The reaction is suitably carried out at a temperature in the range from 0° C. to 150° C., the preferred reaction temperature being from 80° C. to 125° C. as disclosed for example by EP-A 770 615.

Dihalotriazolopyrimidine IV is further reacted with an amine of formula V

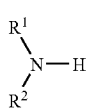

in which $R^1$ and $R^2$ are as defined in formula I to produce compounds of formula I in which X is halogen.

The reaction between the 5,7-dihalo compound IV and the amine of formula V can be carried out under conditions known from WO-A 98/46608. The reaction is preferably carried out in the presence of a solvent. Suitable solvents include ethers, such as dioxane, diethyl ether and, especially, tetrahydrofuran, halogenated hydrocarbons such as dichloromethane and aromatic hydrocarbons, for example toluene.

The reaction is suitably carried out at a temperature in the range from 0° C. to 70° C., the preferred reaction temperature being from 10° C. to 35° C.

It is also preferred that the reaction is carried out in the presence of a base. Suitable bases include tertiary amines, such as triethylamine, and inorganic bases, such as potassium carbonate or sodium carbonate. Alternatively, an excess of the compound of formula V may serve as a base.

Compounds of formula I in which X denotes cyano, $C_1$–$C_6$-alkoxy, $C_1$–$C_6$-haloalkoxy or $C_3$–$C_8$-alkenyloxy can be prepared by reacting compounds I in which X is halogen, preferably chloro, with compounds of formula VI, which are, dependent from the value of X' to be introduced to yield formula I compounds, an an organic cyano salt, an alkoxylate, haloalkoxylate or an alkenyloxylate, respectively, preferably in the presence of a a solvent. The cation M in formula VI has minor influence; for practical and economical reasons usually ammonium-, tetraalkylammonium- or alkalimetal- and earth metal salts are preferred.

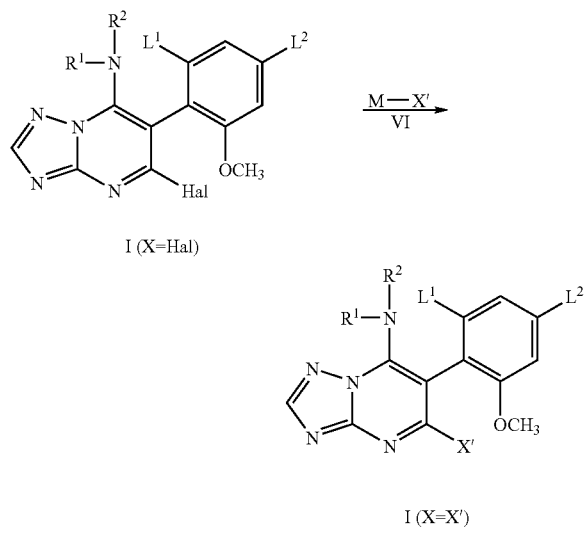

The reaction is suitably carried out at a temperature in the range from 0 to 120° C., the preferred reaction temperature being from 10 to 40° C. [cf. J. Heterocycl. Chem. Vol.12, p. 861–863 (1975)].

Suitable solvents include ethers, such as dioxane, diethyl ether and, especially, tetrahydrofuran, halogenated hydrocarbons such as dichloromethane and aromatic hydrocarbons, for example toluene.

Compounds of formula I in which X denotes $C_1$–$C_6$-alkyl can be prepared by reacting compounds I in which X is halogen, preferably chloro, with malonic acid esters of formula VII, wherein X" denotes H or $C_1$–$C_5$-alkyl and R denotes $C_1$–$C_4$-alkyl, to compounds of formula VIII and decarboxylation under conditions described in U.S. Pat. No. 5,994,360.

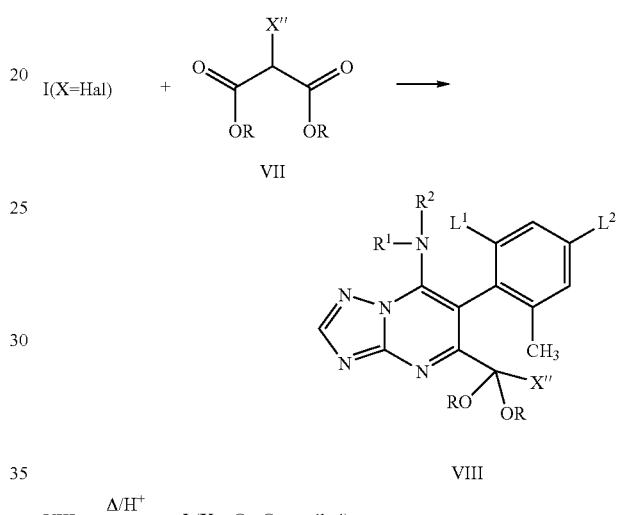

Accordingly, the invention relates to the novel intermediates of formulae II, III and IV.

The compounds of formula II are preferably prepared by reaction of the corresponding substituted bromobenzenes with sodium dial-kylmalonates in the presence of a copper(I) salt [cf. Chemistry Letters, pp. 367–370, 1981; EP-A 10 02 788].

The compounds of formula II may also be prepared by reaction of an alkyl 2-(2-methoxy-phenyl)-acetate with dialkylcarbonate in the presence of a strong base, preferably sodium ethoxide and sodium hydride (cf. Heterocycles, pp. 1031–1047, 1996).

The substituted phenylacetates which are the starting compounds for compounds of formula II are known and commercially available, and/or they are obtainable by generally known methods.

The reaction mixtures are worked up in a customary manner, for example by mixing with water, phase separation and, if required, chromatographic purification of the crude products. Some of the end products are obtained in the form of colorless or slightly brownish, viscous oils, which are purified or freed from volatile components under reduced pressure and at moderately elevated temperatures. If the end products are obtained as solids, purification can also be carried out by recrystallization or digestion.

If individual compounds I are not obtainable by the routes described above, they can be prepared by derivatization of other compounds I.

In the symbol definitions given in the formulae above, collective terms were used which generally represent the following substituents:

halogen: fluorine, chlorine, bromine and iodine;

$C_1$–$C_{10}$-alkyl: saturated, straight-chain or branched hydrocarbon radicals having 1 to 10, especially 1 to 6 carbon atoms, for example $C_1$–$C_4$-alkyl as mentioned above or pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_2$–$C_{10}$-alkenyl: unsaturated, straight-chain or branched hydrocarbon radicals having 2 to 10, especially 2 to 6 carbon atoms and a double bond in any position, for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl; $C_2$–$C_{10}$-alkynyl: straight-chain or branched hydrocarbon radicals having 2 to 10, especially 2 to 4 carbon atoms and a triple bond in any position, for example ethynyl, 1-propynyl, 2-propynyl, 1-butynyl, 2-butynyl, 3-butynyl and 1-methyl-2-propynyl;

$C_1$–$C_{10}$-haloalkyl and haloalkyl moieties of $C_1$–$C_6$-haloalkoxy: straight-chain or branched alkyl groups having 1 to 6 or 10, preferably 1 to 4 carbon atoms (as mentioned above), where the hydrogen atoms in these groups may be partially or fully replaced by halogen atoms as mentioned above, for example $C_1$–$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy;

$C_3$–$C_{10}$-cycloalkyl: mono- or bicyclic cycloalkyl groups having 3 to 10 carbon atoms; monocyclic groups preferably have 3 to 8, especially 3 to 6 ring members, bicyclic groups preferably have 8 to 10 ring members.

A 5- or 6-membered heterocyclyl group, containing one to four nitrogen atoms or one to three nitrogen atoms and one sulfur or oxygen atom, preferably one oxygen atom, for example 1-pyrimidinyl, 2-pyrimidinyl, morpholin-4-yl.

5-membered heteroaryl, containing one to four nitrogen atoms or one to three nitrogen atoms and one sulfur or oxygen atom: 5-membered heteroaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl, containing one to four nitrogen atoms: 6-membered heteroaryl groups which, in addition to carbon atoms, may contain one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

With respect to their intended use, preference is given to triazolopyrimidines of the formula I having the following substituents, where the preference is valid in each case on its own or in combination:

A preferred cycloalkyl moiety is cyclopentyl being optionally substituted by one or more nitro, cyano, $C_1$–$C_6$-alkyl, $C_1$–$C_6$-alkoxy groups.

A preferred heteroaryl moiety is pyridyl, pyrimidyl, pyrazolyl or thienyl.

Preference is given to compounds of formula I in which any alkyl or haloalkyl part of the groups $R^1$ or $R^2$, which may be straight chained or branched, contains up to 10 carbon atoms, preferably 1 to 9 carbon atoms, more preferably 2 to 6 carbon atoms, any alkenyl or alkynyl part of the substituents $R^1$ or $R^2$ contains up to 10 carbon atoms, preferably 2 to 9 carbon atoms, more preferably 3 to 6 carbon atoms, any cycloalkyl part of the substituents $R^1$ or $R^2$ contains from 3 to 10 carbon atoms, preferably from 3 to 8 carbon atoms, more preferably from 3 to 6 carbon atoms, and any bicycloalkyl part of the substituents $R^1$ or $R^2$ contains from 5 to 9 carbon atoms, preferably from 7 to 9 carbon atoms. Any alkyl, alkenyl or alkynyl group may be linear or branched.

Likewise, preference is given to compounds of formula I wherein $R^1$ is not hydrogen.

Compounds of formula I are preferred in which $R^1$ represents a straight-chained or branched $C_1$–$C_{10}$-alkyl, in particular a branched $C_3$–$C_{10}$-alkyl group, a $C_3$–$C_8$-cycloalkyl, a $C_5$–$C_9$-bicycloalkyl, a $C_3$–$C_8$-cycloalkyl-$C_1$–$C_6$-alkyl, $C_1$–$C_{10}$-alkoxy-$C_1$–$C_6$-alkyl, a $C_1$–$C_{10}$-haloalkyl or a phenyl group being optionally substituted by one to three halogen atoms or $C_1$–$C_{10}$-alkyl or $C_1$–$C_{10}$-alkoxy groups.

Particular preference is given to compounds I in which $R^2$ represents hydrogen, $C_1$–$C_{10}$-alkyl or $C_1$–$C_{10}$-haloalkyl, in particular hydrogen.

Besides, particular preference is given to compounds I in which $R^2$ is hydrogen.

Moreover, particular preference is given to compounds I in which $R^2$ is methyl.

Furthermore, particular preference is given to compounds I in which $R^2$ is ethyl.

If $R^1$ denotes $C_1$–$C_{10}$-haloalkyl, preferably polyfluorinated alkyl, in particular 2,2,2-trifluoroethyl, 2-(1,1,1-trifluoropropyl) or 2-(1,1,1-trifluorobutyl), $R^2$ preferably represents hydrogen.

If $R^1$ denotes optionally substituted $C_3$–$C_8$-cycloalkyl, preferably cyclopentyl or cyclohexyl, $R^2$ preferably represents hydrogen or $C_1$–$C_6$-alkyl.

Moreover, particular preference is given to compounds I in which $R^1$ and $R^2$ together with the interjacent nitrogen atom form an optionally substituted heterocyclic ring, preferably an optionally substituted $C_3$–$C_7$-heterocyclic ring, in particular pyrrolidine, piperidine, tetrahydropyridine, in particular 1,2,3,6-tetrahydropyridine or azepane which is optionally substituted by one or more $C_1$–$C_{10}$-alkyl groups.

Preference is given to compounds of formula I in which any alkyl part of the groups $R^1$ or $R^2$, which may be straight chained or branched, contains 1 to 9 carbon atoms, more preferably 2 to 6 carbon atoms, any alkenyl or alkynyl part of the substituents $R^1$ or $R^2$ contains 2 to 9 carbon atoms, more preferably 3 to 6 carbon atoms, any cycloalkyl part of the substituents $R^1$ or $R^2$ contains from 3 to 10 carbon atoms, preferably from 3 to 8 carbon atoms, more preferably from 3 to 6 carbon atoms, and any bicycloalkyl part of the substituents $R^1$ or $R^2$ contains from 7 to 9 carbon atoms. Any alkyl, alkenyl or alkynyl moiety may be linear or branched.

Compounds of formula I are preferred in which $R^1$ represents a straight-chained or branched $C_1$–$C_{10}$-alkyl, in particular branched $C_3$–$C_{10}$-alkyl, a $C_3$–$C_8$-cycloalkyl, $C_5$–$C_9$-bicycloalkyl, $C_3$–$C_8$-cycloalkyl-$C_1$–$C_6$-alkyl, $C_1$–$C_{10}$-alkoxy-$C_1$–$C_6$-alkyl, or phenyl being optionally substituted by one to three $C_1$–$C_{10}$-alkyl or $C_1$–$C_{10}$-alkoxy groups.

Compounds of formula I are preferred wherein not $R^1$ and $R^2$ both are hydrogen.

Particular preference is given to compounds I in which $R^2$ represents hydrogen or $C_1$–$C_{10}$-alkyl, in particular hydrogen.

Moreover, particular preference is given to compounds I in which $R^2$ is methyl or ethyl.

If $R^1$ denotes an optionally substituted $C_3$–$C_8$-cycloalkyl group, preferably cyclopentyl or cyclohexyl, $R^2$ preferably represents hydrogen or $C_1$–$C_6$-alkyl.

Moreover, particular preference is given to compounds I in which $R^1$ and $R^2$ together with the interjacent nitrogen atom form an optionally substituted heterocyclic ring, preferably an optionally substituted $C_3$–$C_7$-heterocyclic ring, in particular a pyrrolidine, piperidine, tetrahydropyridine, in particular 1,2,3,6-tetrahydropyridine or azepane ring which is optionally substituted by one or more $C_1$–$C_{10}$-alkyl groups.

Likewise, particular preference is given to compounds I in which $R^2$ is hydrogen.

Furthermore, preference is given to compounds I in which $L^1$ is fluoro or chloro, particularly fluoro.

Besides, particular preference is given to compounds I in which $L^2$ is hydrogen, chloro or fluoro, particularly fluoro.

Likewise, particular preference is given to compounds I in which $L^1$ is fluoro and $L^2$ is hydrogen.

Particular preference is also given to compounds I in which $L^1$ and $L^2$ both are fluoro.

Moreover, particular preference is also given to compounds I in which $L^1$ and/or $L^2$ is methyl.

Besides, particular preference.is given to compounds I in which X is chloro or bromo, especially chloro.

Moreover, preference is given to compounds I in which X is cyano or methyl.

Furthermore, particular preference is given to compounds I in which X is methoxy, ethoxy, n-propoxy, iso-propoxy, allyloxy, or 3-methylallyloxy.

The particularly preferred embodiments of the intermediates with respect to the variables correspond to those of the radicals X, $R^1$, $R^2$, $L^1$ and $L^2$ of formula I.

Included in the scope of the present invention are (R) and (S) isomers of compounds of general formula I having a chiral center and the racemates thereof, and salts, N-oxides and acid addition compounds.

With respect to their use, particular preference is given to the compounds I compiled in the tables below. The groups mentioned in the tables for a substituent are furthermore for their part, independently of the combination in which they are mentioned, a particularly preferred embodiment of the respective substituents.

Table 1
Compounds of the formula I, in which X is chloro, $L^1$ is hydrogen, $L^2$ is fluoro and $R^1$ and $R^2$ correspond to one row in Table A Table 2
Compounds of the formula I, in which X is chloro, $L^1$ is hydrogen, $L^2$ is chloro and $R^1$ and $R^2$ correspond to one row in Table A Table 3
Compounds of the formula I, in which X is chloro, $L^1$ is fluoro, $L^2$ is hydrogen and $R^1$ and $R^2$ correspond to one row in Table A Table 4
Compounds of the formula I, in which X is chloro, $L^1$ is fluoro, $L^2$ is chloro and $R^1$ and $R^2$ correspond to one row in Table A Table 5
Compounds of the formula I, in which X is chloro, $L^1$ and $L^2$ are fluoro and $R^1$ and $R^2$ correspond to one row in Table A Table 6
Compounds of the formula I, in which X is chloro, $L^1$ is chloro, $L^2$ is hydrogen and $R^1$ and $R^2$ correspond to one row in Table A Table 7
Compounds of the formula I, in which X is chloro, $L^1$ and $L^2$ are chloro and $R^1$ and $R^2$ correspond to one row in Table A Table 8
Compounds of the formula I, in which X is chloro, $L^1$ is chloro, $L^2$ is fluoro and $R^1$ and $R^2$ correspond to one row in Table A Table 9
Compounds of the formula I, in which X is bromo, $L^1$ is hydrogen, $L^2$ is fluoro and $R^1$ and $R^2$ correspond to one row in Table A Table 10
Compounds of the formula I, in which X is bromo, $L^1$ is hydrogen, $L^2$ is chloro and $R^1$ and $R^2$ correspond to one row in Table A Table 11
Compounds of the formula I, in which X is bromo, $L^1$ is fluoro, $L^2$ is hydrogen and $R^1$ and $R^2$ correspond to one row in Table A Table 12
Compounds of the formula I, in which X is bromo, $L^1$ is fluoro, $L^2$ is chloro and $R^1$ and $R^2$ correspond to one row in Table A Table 13
Compounds of the formula I, in which X is bromo, $L^1$ and $L^2$ are fluoro and $R^1$ and $R^2$ correspond to one row in Table A Table 14
Compounds of the formula I, in which X is bromo, $L^1$ is chloro, $L^2$ is hydrogen and $R^1$ and $R^2$ correspond to one row in Table A Table 15
Compounds of the formula I, in which X is bromo, $L^1$ and $L^2$ are chloro and $R^1$ and $R^2$ correspond to one row in Table A Table 16
Compounds of the formula I, in which X is bromo, $L^1$ is chloro, $L^2$ is fluoro and $R^1$ and $R^2$ correspond to one row in Table A Table 17

Compounds of the formula I, in which X is cyano, $L^1$ is hydrogen, $L^2$ is fluoro and $R^1$ and $R^2$ correspond to one row in Table A Table 18

Compounds of the formula I, in which X is cyano, $L^1$ is hydrogen, $L^2$ is chloro and $R^1$ and $R^2$ correspond to one row in Table A Table 19

Compounds of the formula I, in which X is cyano, $L^1$ is fluoro, $L^2$ is hydrogen and $R^1$ and $R^2$ correspond to one row in Table A Table 20

Compounds of the formula I, in which X is cyano, $L^1$ is fluoro, $L^2$ is chloro and $R^1$ and $R^2$ correspond to one row in Table A Table 21

Compounds of the formula I, in which X is cyano, $L^1$ and $L^2$ are fluoro and $R^1$ and $R^2$ correspond to one row in Table A Table 22

Compounds of the formula I, in which X is cyano, $L^1$ is chloro, $L^2$ is hydrogen and $R^1$ and $R^2$ correspond to one row in Table A Table 23

Compounds of the formula I, in which X is cyano, $L^1$ and $L^2$ are chloro and $R^1$ and $R^2$ correspond to one row in Table A Table 24

Compounds of the formula I, in which X is cyano, $L^1$ is chloro, $L^2$ is fluoro and $R^1$ and $R^2$ correspond to one row in Table A Table 25

Compounds of the formula I, in which X is methoxy, $L^1$ is hydrogen, $L^2$ is fluoro and $R^1$ and $R^2$ correspond to one row in Table A Table 26

Compounds of the formula I, in which X is methoxy, $L^1$ is hydrogen, $L^2$ is chloro and $R^1$ and $R^2$ correspond to one row in Table A Table 27

Compounds of the formula I, in which X is methoxy, $L^1$ is fluoro, $L^2$ is hydrogen and $R^1$ and $R^2$ correspond to one row in Table A Table 28

Compounds of the formula I, in which X is methoxy, $L^1$ is fluoro, $L^2$ is chloro and $R^1$ and $R^2$ correspond to one row in Table A Table 29

Compounds of the formula I, in which X is methoxy, $L^1$ and $L^2$ are fluoro and $R^1$ and $R^2$ correspond to one row in Table A Table 30

Compounds of the formula I, in which X is methoxy, $L^1$ is chloro, $L^2$ is hydrogen and $R^1$ and $R^2$ correspond to one row in Table A Table 31

Compounds of the formula I, in which X is methoxy, $L^1$ and $L^2$ are chloro and $R^1$ and $R^2$ correspond to one row in Table A Table 32

Compounds of the formula I, in which X is methoxy, $L^1$ is chloro, $L^2$ is fluoro and $R^1$ and $R^2$ correspond to one row in Table A Table 33

Compounds of the formula I, in which X is methyl, $L^1$ is hydrogen, $L^2$ is fluoro and $R^1$ and $R^2$ correspond to one row in Table A Table 34

Compounds of the formula I, in which X is methyl, $L^1$ is hydrogen, $L^2$ is chloro and $R^1$ and $R^2$ correspond to one row in Table A Table 35

Compounds of the formula I, in which X is methyl, $L^1$ is fluoro, $L^2$ is hydrogen and $R^1$ and $R^2$ correspond to one row in Table A Table 36

Compounds of the formula I, in which X is methyl, $L^1$ is fluoro, $L^2$ is chloro and $R^1$ and $R^2$ correspond to one row in Table A Table 37

Compounds of the formula I, in which X is methyl, $L^1$ and $L^2$ are fluoro and $R^1$ and $R^2$ correspond to one row in Table A Table 38

Compounds of the formula I, in which X is methyl, $L^1$ is chloro, $L^2$ is hydrogen and $R^1$ and $R^2$ correspond to one row in Table A Table 39

Compounds of the formula I, in which X is methyl, $L^1$ and $L^2$ are chloro and $R^1$ and $R^2$ correspond to one row in Table A Table 40

Compounds of the formula I, in which X is methyl, $L^1$ is chloro, $L^2$ is fluoro and $R^1$ and $R^2$ correspond to one row in Table A

TABLE A

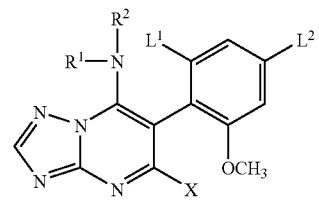

I

| No. | $R^1$ | $R^2$ |
|---|---|---|
| A-1 | H | H |
| A-2 | $CH_2CH_3$ | H |
| A-3 | $CH_2CH_3$ | $CH_3$ |
| A-4 | $CH_2CH_3$ | $CH_2CH_3$ |
| A-5 | $CH_2CF_3$ | H |
| A-6 | $CH_2CF_3$ | $CH_3$ |
| A-7 | $CH_2CF_3$ | $CH_2CH_3$ |
| A-8 | $CH_2CCl_3$ | H |
| A-9 | $CH_2CCl_3$ | $CH_3$ |
| A-10 | $CH_2CCl_3$ | $CH_2CH_3$ |
| A-11 | $CH_2CH_2CH_3$ | H |

TABLE A-continued $$\text{Structure I: } R^1R^2N-\text{(pyrimidine-triazole core with } L^1, L^2, OCH_3, X \text{ substituents)}$$

| No. | R¹ | R² |
|---|---|---|
| A-12 | CH$_2$CH$_2$CH$_3$ | CH$_3$ |
| A-13 | CH$_2$CH$_2$CH$_3$ | CH$_2$CH$_3$ |
| A-14 | CH$_2$CH$_2$CH$_3$ | CH$_2$CH$_2$CH$_3$ |
| A-15 | CH(CH$_3$)$_2$ | H |
| A-16 | CH(CH$_3$)$_2$ | CH$_3$ |
| A-17 | CH(CH$_3$)$_2$ | CH$_2$CH$_3$ |
| A-18 | (±) CH(CH$_3$)—CH$_2$CH$_3$ | H |
| A-19 | (±) CH(CH$_3$)—CH$_2$CH$_3$ | CH$_3$ |
| A-20 | (±) CH(CH$_3$)—CH$_2$CH$_3$ | CH$_2$CH$_3$ |
| A-21 | (S) CH(CH$_3$)—CH$_2$CH$_3$ | H |
| A-22 | (S) CH(CH$_3$)—CH$_2$CH$_3$ | CH$_3$ |
| A-23 | (S) CH(CH$_3$)—CH$_2$CH$_3$ | CH$_2$CH$_3$ |
| A-24 | (R) CH(CH$_3$)—CH$_2$CH$_3$ | H |
| A-25 | (R) CH(CH$_3$)—CH$_2$CH$_3$ | CH$_3$ |
| A-26 | (R) CH(CH$_3$)—CH$_2$CH$_3$ | CH$_2$CH$_3$ |
| A-27 | (±) CH(CH$_3$)—CH(CH$_3$)$_2$ | H |
| A-28 | (±) CH(CH$_3$)—CH(CH$_3$)$_2$ | CH$_3$ |
| A-29 | (±) CH(CH$_3$)—CH(CH$_3$)$_2$ | CH$_2$CH$_3$ |
| A-30 | (S) CH(CH$_3$)—CH(CH$_3$)$_2$ | H |
| A-31 | (S) CH(CH$_3$)—CH(CH$_3$)$_2$ | CH$_3$ |
| A-32 | (S) CH(CH$_3$)—CH(CH$_3$)$_2$ | CH$_2$CH$_3$ |
| A-33 | (R) CH(CH$_3$)—CH(CH$_3$)$_2$ | H |
| A-34 | (R) CH(CH$_3$)—CH(CH$_3$)$_2$ | CH$_3$ |
| A-35 | (R) CH(CH$_3$)—CH(CH$_3$)$_2$ | CH$_2$CH$_3$ |
| A-36 | (±) CH(CH$_3$)—C(CH$_3$)$_3$ | H |
| A-37 | (±) CH(CH$_3$)—C(CH$_3$)$_3$ | CH$_3$ |
| A-38 | (±) CH(CH$_3$)—C(CH$_3$)$_3$ | CH$_2$CH$_3$ |
| A-39 | (S) CH(CH$_3$)—C(CH$_3$)$_3$ | H |
| A-40 | (S) CH(CH$_3$)—C(CH$_3$)$_3$ | CH$_3$ |
| A-41 | (S) CH(CH$_3$)—C(CH$_3$)$_3$ | CH$_2$CH$_3$ |
| A-42 | (R) CH(CH$_3$)—C(CH$_3$)$_3$ | H |
| A-43 | (R) CH(CH$_3$)—C(CH$_3$)$_3$ | CH$_3$ |
| A-44 | (R) CH(CH$_3$)—C(CH$_3$)$_3$ | CH$_2$CH$_3$ |
| A-45 | (±) CH(CH$_3$)—CF$_3$ | H |
| A-46 | (±) CH(CH$_3$)—CF$_3$ | CH$_3$ |
| A-47 | (±) CH(CH$_3$)—CF$_3$ | CH$_2$CH$_3$ |
| A-48 | (S) CH(CH$_3$)—CF$_3$ | H |
| A-49 | (S) CH(CH$_3$)—CF$_3$ | CH$_3$ |
| A-50 | (S) CH(CH$_3$)—CF$_3$ | CH$_2$CH$_3$ |
| A-51 | (R) CH(CH$_3$)—CF$_3$ | H |
| A-52 | (R) CH(CH$_3$)—CF$_3$ | CH$_3$ |
| A-53 | (R) CH(CH$_3$)—CF$_3$ | CH$_2$CH$_3$ |
| A-54 | (±) CH(CH$_3$)—CCl$_3$ | H |
| A-55 | (±) CH(CH$_3$)—CCl$_3$ | CH$_3$ |
| A-56 | (±) CH(CH$_3$)—CCl$_3$ | CH$_2$CH$_3$ |
| A-57 | (S) CH(CH$_3$)—CCl$_3$ | H |
| A-58 | (S) CH(CH$_3$)—CCl$_3$ | CH$_3$ |
| A-59 | (S) CH(CH$_3$)—CCl$_3$ | CH$_2$CH$_3$ |
| A-60 | (R) CH(CH$_3$)—CCl$_3$ | H |
| A-61 | (R) CH(CH$_3$)—CCl$_3$ | CH$_3$ |
| A-62 | (R) CH(CH$_3$)—CCl$_3$ | CH$_2$CH$_3$ |
| A-63 | CH$_2$C(CH$_3$)=CH$_2$ | H |
| A-64 | CH$_2$C(CH$_3$)=CH$_2$ | CH$_3$ |
| A-65 | CH$_2$C(CH$_3$)=CH$_2$ | CH$_2$CH$_3$ |
| A-66 | cyclopentyl | H |
| A-67 | cyclopentyl | CH$_3$ |
| A-68 | cyclopentyl | CH$_2$CH$_3$ |
| A-69 | —(CH$_2$)$_2$CH(CH$_3$)(CH$_2$)$_2$— | |

The compounds I are suitable as fungicides. They have outstanding activity against a broad spectrum of phytopathogenic fungi, in particular from the classes of the *Ascomycetes, Deuteromycetes, Phycomycetes* and *Basidiomycetes*. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

*Alternaria* species, *Podosphaera* species, *Sclerotinia* species, *Physalospora* canker on vegetables and fruit,

*Botrytis* cinerea (gray mold) an strawberries, vegetables, ornamentals and grapevines,

*Corynespora cassiicola* on cucumbers,

*Colletotrichum* species on fruit and vegetables,

*Diplocarpon rosae* on roses,

*Elsinoe fawcetti* and *Diaporthe citri* on citrus fruit,

*Sphaerotheca* species on cucurbits, strawberries and roses,

*Cercospora* species on peanuts, sugar beets and aubergines,

*Erysiphe cichoracearum* on cucurbits,

*Leveillula taurica* on paprika, tomatoes and aubergines,

*Mycosphaerella* species on apples and japanese apricot,

*Phyllactinia kakicola, Gloesporium kaki* on japanese apricot,

*Gymnosporangium yamadae, Leptothyrium pomi, Podosphaera leucotricha* and *Gloedes pomigena* on apples,

*Cladosporium carpophilum* on pears and japanese apricot,

*Phomopsis* species on pears,

*Phytophthora* species on citrus fruit, potatoes, onions, especially *Phytophthora infestans* on potatoes and tomatoes,

*Blumeria graminis* (powdery mildew) on cereals,

*Fusarium*- and *Verticillium* species on various plants,

*Glomerella cingulata* on tee,

*Drechslera*- and *Bipolaris* species on cereals and rice,

*Mycosphaerella* species on bananas and peanuts,

*Plasmopara viticola* on grapevines,

*Personospora* species on onions, spinach and chrysantemum,

*Phaeoisariopsis vitis* and *Sphaceloma ampelina* on grapefruits,

*Pseudocercosporella herpotrichoides* on wheat and barley,

*Pseudoperonospora* species on hop and cucumbers,

*Puccinia* species and *Typhula* species on cereals and turf,

*Pyricularia oryzae* on rice,

*Rhizoctonia* species on cotton, rice and turf,

*Stagonospora nodorum* and *Septoria tritici* on wheat,

*Uncinula necator* on grapevines,

*Ustilago* species on cereals and sugar cane, and

*Venturia* species (scab) on apples and pears.

Moreover, the compounds I are suitable for controlling harmful fungi such as *Paecilomyces variotii* in the protection of materials (e.g. wood, paper, paint dispersions, fibers and tissues) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

The compounds I can be converted into the customary formulations, e.g. solutions, emulsions, suspensions, dusts, powders, pastes and granules. The use form depends on the particular purpose; in any case, it should guarantee a fine and uniform distribution of the compound according to the invention.

The formulations are prepared in a known manner, e.g. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly-disperse silica, silicates); emulsifiers such as non-ionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalene-sulfonic acid, phenolsulfonic acid, dibutylnaphthalene-sulfonic acid, alkylaryl-sulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanone, cyclohexanone, chlorobenzene, isophorone, strongly polar solvents, e.g. dimethylformamide, dimethyl sulfoxide, N-methylpyrrolidone and water.

Powders, materials for scattering and dusts can be prepared by mixing or concomitantly grinding the active substances with a solid carrier.

Granules, e.g. coated granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise of from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diiso-butylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, scattering or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides, fungicides, other pesticides, or bactericides may be added to the active ingredients, if appropriate also only immediately prior to use (tank mix). These agents can be admixed with the agents according to the invention in a weight ratio of 1:10 to 10:1.

In the use form as fungicides, the compositions according to the invention can also be present together with other active ingredients, e.g. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides, together with which the compounds according to the invention can be used, is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebis-dithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[(bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1, 1,2,2-tetrachloroethylthio)tetrahydrophthalimide, N-trichloromethylthiotetrahydrophthalimide, N-trichloromethylthiophthalimide, 5-Chloro-2-cyano-4-p-tolyl-imidazole-1-sulfonic acid dimethylamide, N-dichlorofluoromethylthio-N',N'-dimethyl-N-phenylsulfo-diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2-Chloro-N-(4'-chloro-biphenyl-2-yl)-nicotinamide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane; 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethyl-morpholine, N-[3-(p-tert-butylphenyl)-2-methylpropyl]-piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolyl-urea, 1-(4-chlorophenoxy)-3,3-dimethyl-1-(1H-1,2,4-triazol-1-yl)-2-butanone, 1-(4-chlorophenoxy)-3,3-dimethyl-1-(1H-1, 2,4-triazol-1-yl)-2-butanol, (2RS,3RS)-1-[3-(2-chlorophenyl)-2-(4-fluorophenyl)-oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurines such as azoxystrobin, kresoxim methyl, methyl-E-methoxyimino-[α-(2-phenoxyphenyl)]-acetamide, methyl E-methoxyimino-[α-(2,5-dimethylphenoxy)-o-tolyl]acetamide, picoxystrobin, pyraclostrobin, trifloxystrobin, anilinopyrimidines such as N-(4,6-dimethylpyrimidin-2-yl)aniline, N-[4-methyl-6-(1-propynyl)pyrimidin-2-yl]-aniline, N-[4-methyl-6-cyclopropylpyrimidin-2-yl]aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxy-phenyl)acryloylmorpholine, 3-(4-fluorophenyl)-3-(3,4-dimethoxy-phenyl)acryloylmorpholine, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-amino-butyrolactone, DL-N-(2,6-dimethylphenyl)-N-(phenylacetyl)alanine methyl ester, 5-methyl-5-vinyl-3-(3,5-dichlorophenyl)-2,4-di-oxo-1,3-oxazolidine, 3-[3,5-dichlorophenyl(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 3,5-Dichloro-N-(3-chloro-1-ethyl-1-methyl-2-oxo-propyl)-4-methyl-benzamide, 1-(3-Bromo-6-methoxy-2-methyl-phenyl)-1-(2,3,4-trimethoxy-6-methyl-phenyl)-methanone, 1-[2-(2,4-dichloro-phenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

Synthesis Examples

With due modification of the starting compounds, the protocols shown in the synthesis examples below were used for obtaining further compounds I.

EXAMPLE 1

Preparation of diethyl (4,6-difluoro-2-methoxyphenyl)-malonate

Diethyl malonate (0.49 mol) was added to a mixture of sodium hydride (0.51 mol) and 1,4-dioxane (140 ml) at 60° C. within 2 hours. The mixture was stirred for 10 minutes at 60° C. and copper (I) bromide (0.05 mol) was added. After 15 minutes, a mixture of 2-methoxy-4,6-difluorobromobenzene (0.25 mol) and 1,4-dioxane (10 ml) was added. The reaction mixture was stirred at about 100° C. for about 15 hours. After cooling to about 15 to 20° C. 35 ml of 12N hydrochloric acid were added. The precipitate was filtered off. The filtrate was extracted with diethyl ether. The organic phase was separated, dried and filtered. The filtrate was evaporated to yield 44 g of the title compound.

EXAMPLE 2

Preparation of 5,7-dihydroxy-6-(4,6-difluoro-2-methoxyphenyl)-[1,2,4]-triazolo-[1,5-α]pyrimidine A mixture of 3-amino-1,2,4-triazole (14 g), 0.17 mmol of the malonate from Ex. 1 and tributylamine (50 ml) was stirred at 180° C. for six hours. After cooling to 70° C. a solution of 21 g sodium hydroxide in 200 ml water was added and the reaction mixture was stirred for 30 minutes. The phases were separated and the aqueous phase was extracted with diethyl ether. The aqueous phase was acidified with concentrated hydrochloric acid. The precipitate was collected by filtration and dried to yield 39 g of the title compound.

EXAMPLE 3

Preparation of 5,7-dichloro-6-(4,6-difluoro-2-methoxyphenyl)-[1,2,4]-triazolo-[1,5-α]pyrimidine A mixture of 30 g of the product from Ex. 2 and phosphorous oxychloride (50 ml) was refluxed for eight hours. Phosphorous oxychloride was partly distilled off. The residue was poured into a mixture of dichloromethane and water. The organic layer was separated, dried and filtered. The filtrate was concentrated to yield 29 g of the title compound of mp. 122° C.

EXAMPLE 4

Preparation of 5-chloro-6-(4,6-difluoro-2-methoxyphenyl)-7-(1,1,1-trifluoroprop-2-yl)amino-[1,2,4]-triazolo[1,5-α]pyrimidine [I-38]

A mixture of (1,1,1-trifluoroprop-2-yl)amine (7.5 mmol) and 1.5 mmol of the product from Ex. 3 was stirred for 16 hours at about 40° C. and subsequently washed with 5% hydrocloric acid. The organic layer was separated, dried and filtered. The filtrate was evaporated and the residue was chromatographed to yield 0.41 g of two separable rotamers of the title compound of mp. 181° C., and IR 1617, 1553, 1099 cm$^{-1}$, resp.

EXAMPLE 5

Preparation of 5-cyano-6-(6-fluoro-2-methoxyphenyl)-7-diethylamino-[1,2,4]-triazolo[1,5-α]pyrimidine [I-42]

A mixture of 0.1 mol of compound [I-5] and (0.25 mol) tetraethyl-ammonium cyanide in 750 ml Dimethylformamide (DMF) was stirred for 16 hours at 20 to 25° C. Water and methyl-tert.butylether (MTBE) were added to this mix ture, the organic phase was separated, washed with water and dried. The solvent was evaporated under reduced pressure and the residue was purified through column chromatography to yield 5.93 g of the title compound of mp. 135° C.

EXAMPLE 6

Preparation of 5-methoxy-6-(6-fluoro-2-methoxyphenyl)-7-diethylamino-[1,2,4]-triazolo[1,5α-]pyrimidine [I-43]

To a solution of 65 mmol of compound [I-5] in 400 ml of dry methanol a solution of sodium methanolate (30%, 71.5 mmol) was added at 20 to 25° C. This mixture was stirred for 16 hours at 20 to 25° C. Methanol was evaporated and the residue was dissolved in dichloromethane. The organic phase was washed with water and dried. The solvent was evaporated under reduced pressure and the residue was purified through column chromatography to yield 4.17 g of the title compound of mp. 114° C.

EXAMPLE 7

Preparation of 5-methyl-6-(6-fluoro-2-methoxyphenyl)-7-diethylamino-[1,2,4]-triazolo[1,5-α]pyrimidine [I-44]

A mixture of 20 ml diethyl malonate and 0.27 g NaH of a 50% dispersion in mineral oil (5.65 mmol) in 50 ml acetonitrile was stirred at at 20 to 25° C. for 2 hours. To this mixture 4.71 mmol of compound [I-5] were added. The reaction mixture was heated to 60° C. and stirred for 20 hours. 50 ml of aqueous ammonium chloride were added and the mixture was acidified with diluted HCl. The reaction mixture was extracted with MTBE. The combined organic phases were dried and concentrated. The residue was purified by column chromatography. The pure product obtained was diluted in concentrated HCl and heated to 80° C. for 24 hours. The reaction mixture was cooled and adjusted to pH 5 by addition of aqueous NaOH. The reaction mixture was extracted with MTBE. The combined organic phases were dried, concentrated and purified by column chromatography to yield 0.72 g of the title compound.

$^1$H-NMR δ [ppm]: 8.33 (s); 7.42 (q); 6.85 (q); 3.80 (s); 3.35 (m); 3.25 (m); 2.27 (s); 0.99 (t).

TABLE I

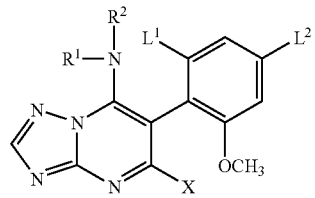

I

| No. | $R^1$ | $R^2$ | $L^1$ | $L^2$ | X | phys. data (m.p. [° C.]; IR [cm$^{-1}$]) |
|---|---|---|---|---|---|---|
| I-1 | CH$_2$C(CH$_3$)=CH$_2$ | CH$_2$CH$_3$ | F | H | Cl | 116 |
| I-2 | CH(CH$_3$)$_2$ | H | F | H | Cl | 119 |
| I-3 | —(CH$_2$)$_2$CH(CH$_3$)(CH$_2$)$_2$— | | F | H | Cl | 87 |
| I-4 | cyclopentyl | H | F | H | Cl | 109 |
| I-5 | CH$_2$CH$_3$ | CH$_2$CH$_3$ | F | H | Cl | 93 |
| I-6 | CH$_2$CH$_2$CH$_3$ | CH$_2$CH$_2$CH$_3$ | F | H | Cl | 109 |
| I-7 | CH(CH$_3$)$_2$ | CH$_3$ | F | H | Cl | 119 |
| I-8 | (±) CH(CH$_3$)—CH$_2$CH$_3$ | H | F | H | Cl | 98 |
| I-9 | (S) CH(CH$_3$)—CH$_2$CH$_3$ | H | F | H | Cl | 112 |
| I-10 | (R) CH(CH$_3$)—CH$_2$CH$_3$ | H | F | H | Cl | 112 |
| I-11 | (±) CH(CH$_3$)—CH(CH$_3$)$_2$ | H | F | H | Cl | 133 |
| I-12 | (S) CH(CH$_3$)—CH(CH$_3$)$_2$ | H | F | H | Cl | 136 |
| I-13 | (R) CH(CH$_3$)—CH(CH$_3$)$_2$ | H | F | H | Cl | 136 |
| I-14 | (±) CH(CH$_3$)—CH(CH$_3$)$_3$ | H | F | H | Cl | 116 |
| I-15 | (S) CH(CH$_3$)—CH(CH$_3$)$_3$ | H | F | H | Cl | 176 |
| I-16 | (R) CH(CH$_3$)—CH(CH$_3$)$_3$ | H | F | H | Cl | 176 |
| I-17 | (±) CH(CH$_3$)—CF$_3$ | H | F | H | Cl | 131 |
| I-18 | (S) CH(CH$_3$)—CF$_3$ | H | F | H | Cl | 107 |
| I-19 | (R) CH(CH$_3$)—CF$_3$ | H | F | H | Cl | 108 |
| I-20 | CH$_2$CF$_3$ | H | F | H | Cl | 182 |
| I-21 | H | H | F | H | Cl | 247 |
| I-22 | CH$_2$C(CH$_3$)=CH$_2$ | CH$_2$CH$_3$ | F | F | Cl | 146 |
| I-23 | CH(CH$_3$)$_2$ | H | F | F | Cl | 1614, 1574, 1097 |
| I-24 | —(CH$_2$)$_2$CH(CH$_3$)(CH$_2$)$_2$— | | F | F | Cl | 1595, 1532, 1096 |
| I-25 | cyclopentyl | H | F | F | Cl | 1612, 1574, 1095 |
| I-26 | CH$_2$CH$_3$ | CH$_2$CH$_3$ | F | F | Cl | 112 |
| I-27 | CH$_2$CH$_2$CH$_3$ | CH$_2$CH$_2$CH$_3$ | F | F | Cl | 98 |
| I-28 | CH(CH$_3$)$_2$ | CH$_3$ | F | F | Cl | 1595, 1526, 1093 |
| I-29 | (±) CH(CH$_3$)—CH$_2$CH$_3$ | H | F | F | Cl | 1613, 1576, 1097 |
| I-30 | (S) CH(CH$_3$)—CH$_2$CH$_3$ | H | F | F | Cl | 1611, 1575, 1097 |
| I-31 | (R) CH(CH$_3$)—CH$_2$CH$_3$ | H | F | F | Cl | 1611, 1576, 1098 |
| I-32 | (±) CH(CH$_3$)—CH(CH$_3$)$_2$ | H | F | F | Cl | A) 1612, 1575, 1098; B) 1611, 1576, 1097 |

TABLE I-continued $$\text{I}$$

[Structure: A triazolopyrimidine with R¹R²N- group at one position, a phenyl group bearing L¹, L², and OCH₃ substituents, and X substituent]

| No. | R¹ | R² | L¹ | L² | X | phys. data (m.p. [° C.]; IR [cm⁻¹]) |
|---|---|---|---|---|---|---|
| I-33 | (S) CH(CH₃)—CH(CH₃)₂ | H | F | F | Cl | A) 1612, 1575, 1098; B) 1611, 1575, 1097 |
| I-34 | (R) CH(CH₃)—CH(CH₃)₂ | H | F | F | Cl | A) 1611, 1575, 1098; B) 1611, 1576, 1097 |
| I-35 | (±) CH(CH₃)—CH(CH₃)₃ | H | F | F | Cl | A) mp. 126; B) 1612, 1575, 1097 |
| I-36 | (S) CH(CH₃)—CH(CH₃)₃ | H | F | F | Cl | A) mp. 145; B) 1610, 1583, 1099 |
| I-37 | (R) CH(CH₃)—CH(CH₃)₃ | H | F | F | Cl | A) mp. 144; B) 1610, 1583, 1099 |
| I-38 | (±) CH(CH₃)—CF₃ | H | F | F | Cl | cf. Example 4 |
| I-39 | (S) CH(CH₃)—CF₃ | H | F | F | Cl | A) mp. 150; B) 1610, 1579, 1097 |
| I-40 | (R) CH(CH₃)—CF₃ | H | F | F | Cl | A) mp. 150; B) 1617, 1554, 1099 |
| I-41 | CH₂CF₃ | H | F | F | Cl | 253 |
| I-42 | CH₂CH₃ | CH₂CH₃ | F | H | CN | 135 |
| I-43 | CH₂CH₃ | CH₂CH₃ | F | H | OCH₃ | 114 |
| I-44 | CH₂CH₃ | CH₂CH₃ | F | H | CH₃ | cf. Example 7 |

In some cases of chiral groups R¹ and due to the hindered rotation of the phenyl group two diastereomers A) and B) exist which may differ in their physical properties.

Examples of the action against harmful fungi

The fungicidal action of the compounds of the formula I was demonstrated by the following experiments:

The active compounds, separately or together, were formulated as a 10% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil) and diluted with water to the desired concentration.

Use Example 1—Fungicidal control of leaf spot on beets (*Cercospora beticola*)

Young sugar beet seedlings of the cultivar "ACH-31" were grown in pots to the 2 to 4 leaf stage. These plants were sprayed to runoff with an aqueous suspension, containing the concentration of active ingredient mentioned in the table below, prepared from a stock solution containing 5% of the active ingredient, 94% cyclohexanone and 1% emulsifier (Tween 20). After the plants had dried (3–5 h), they were inoculated with a spore suspension of *Cercospora beticola* in an aqueous solution of 0.5% gelatine. Then the trial plants were immediately transferred to a humid chamber with 18–23° C. and a relative humidity close to 100% and kept there for 5 days. For a period of further 10–14 days a cultivation in a greenhouse followed at 21–23° C. and a relative humidity about 95%. Then the extent of fungal attack on the leaves was visually assessed as % diseased leaf area.

In this test, the plants which had been treated with 50 and 200 ppm, resp., of the mixture of both rotamers of Example 4 showed an infection of not more than 7%, whereas the untreated plants were infected to 90%.

Use Example 2—Protective action on cucumber mildew

Leaves of pot grown cucumber seedlings of the "Chinesische Schlange" variety were sprayed to runoff with aqueous liquors made from a stock solution consisting of 10% of active ingredient, 85% of cyclohexanone, and 5% of emulsifier. 20 hours after the sprays-on layer had dried, the plants were inoculated with a aqueous spore suspension of cucumber mildew (*Sphaerotheca fuliginea*). The plants were then placed for 7 days in the greenhouse at 20 to 24° C. and a relative humidity of 60 to 80%. The extent of fungus spread was assessed as %-attack of the whole leaf surface.

In this trial, the plants which have been treated with 250 ppm of compounds I-24, I-32B, I-35A, and I-38B, resp., showed no infection, whereas the untreated plants were infected to 90%.

Use Example 3—Action on *Botrytis cinerea* on paprika leaves

Leaves of pot grown paprika seedlings at the four- to five-leave stage of the "Neusiedler Ideal Elite" variety were sprayed to runoff with aqueous liquors made from a stock solution consisting of 10% of active ingredient, 85% of cyclohexanone, and 5% of emulsifier. After 24 hours the plants were inoculated with a spore suspension of the fungus *Botzytis cinerea* (1.7×10⁶ spores per ml of a 2% strength biomalt solution) and kept for 5 days at 20 to 24° C. and a high relative humidity. Assessment was visual.

In this trial, the plants which have been treated with 250 ppm of compounds I-24, and I-29, resp., showed no infection, whereas the untreated plants were infected to 85%.

Use Example 4—Action on *Alternaria solani* in tomatoes

Leaves of pot grown tomato seedlings of the "Große Fleischtomate St. Pierre" variety were sprayed with aqueous liquors made from a stock solution consisting of 10% of active ingredient, 85% of cyclohexanone, and 5% of emulsifier. After 24 hours the leaves were infected with a zoospore suspension of *Alternaria solani* (1.7×10⁶ spores per ml of a 2% strength biomalt solution). The plants were then placed in a water vapour-saturated chamber at 20 to 22° C. After 5 days the disease had spread to such a great extent on the untreated plants that the fungicidal activity of the substances could be assessed.

In this trial, the plants which have been treated with 250 ppm of compounds I-32B, and I-35A, resp., showed an infection of not more than 7%, whereas the untreated plants were infected to 90%.

The invention claimed is:

1. Substituted 6-(2-methoxy-phenyl)-triazolopyrimidines of formula I

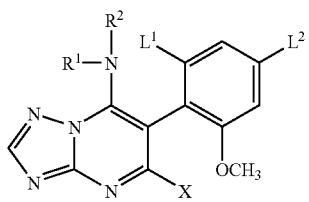

in which
R¹ and R² independently denote hydrogen or $C_1$–$C_{10}$-alkyl, $C_2$–$C_{10}$-alkenyl, $C_2$–$C_{10}$-alkynyl, or $C_4$–$C_{10}$-alkadienyl, $C_1$–$C_{10}$-haloalkyl, $C_2$–$C_{10}$-haloalkenyl, $C_3$–$C_{10}$-cycloalkyl, phenyl, naphthyl, or $C_3$–$C_{10}$-cycloalkyl, phenyl, naphthyl, or 5- or 6-membered heterocyclyl, containing one to four nitrogen atoms or one to three nitrogen atoms and one sulfur or oxygen atom, or 5- or 6-membered heteroaryl, containing one to four nitrogen atoms or one to three nitrogen atoms and one sulfur or oxygen atom, or where R¹ and R² radicals may be unsubstituted or partly or fully halogenated or may carry one to three groups $R^a$, $R^a$ is cyano, nitro, hydroxyl, $C_1$–$C_6$-alkyl, $C_1$–$C_6$-haloalkyl, $C_3$–$C_6$-cycloalkyl, $C_1$–$C_6$-alkoxy, $C_1$–$C_6$-haloalkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkynyl, $C_3$–$C_6$-alkynyloxy and $C_1$–$C_4$-alkylenedioxy; or R¹ and R² together with the interjacent nitrogen atom represent a 5- or 6-membered heterocyclic ring, containing one to four nitrogen atoms or one to three nitrogen atoms and one sulfur or oxygen atom, which may be substituted by one to three $R^a$ radicals;

L¹, L² independently denote hydrogen or halogen, provided that at least one from L¹ or L² is halogen;

X is halogen, cyano, $C_1$–$C_6$-alkyl, $C_1$–$C_6$-alkoxy, $C_1$–$C_6$-haloalkoxy or $C_3$–$C_8$-alkenyloxy.

2. Compounds of formula I according to claim 1, in which R¹ is straight chained or branched $C_1$–$C_6$-alkyl, $C_2$–$C_6$-alkenyl, $C_3$–$C_9$-cycloalkyl, or $C_1$–$C_{10}$-haloalkyl, and R² is hydrogen or $C_1$–$C_6$-alkyl, or R¹ and R² together with the interjacent nitrogen atom represent a heterocyclic ring with 5 or 6 carbon atoms being optionally substituted with one or two $C_1$–$C_6$-alkyl groups.

3. Compounds according to claim 1 in which R² is hydrogen.

4. Compounds according to claim 1 in which X is halogen.

5. A process for the preparation of compounds of formula I as defined in claim 4 which comprises reacting 5-amino-1,2,4-triazole

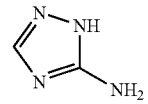

with 2-phenyl-substituted malonic acid ester of formula II,

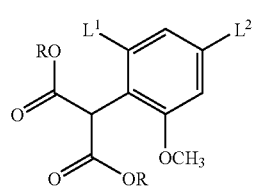

wherein L¹ and L² are as defined in formula I, and R denotes $C_1$–$C_6$-alkyl, under alkaline conditions, to yield compounds of formula III,

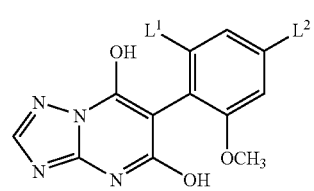

which are subsequently treated with a halogenating agent to give 5,7-dihalogen-6-phenyl-triazolopyrimidines of formula IV

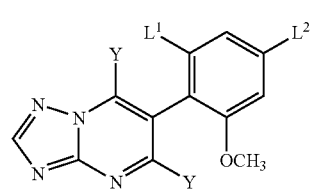

in which Y is halogen with an amine of formula V

in which R¹ and R² are as defined in formula I to produce compounds of formula I.

6. A process for the preparation of compounds of formula I according to claim 1 wherein X is cyano, $C_1$–$C_{10}$-alkoxy, or $C_1$–$C_{10}$-haloalkyl, which comprises reacting 5-halogen-triazolopyrimidine of formula I

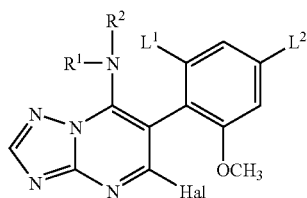 I(X=Hal)

with compounds of formula VI,

M-X'  VI which are, dependent from the value of X' to be introduced, an anorganic cyano salt, an alkoxylate, haloalkoxylate or an alkenyloxylate, resp., wherein M is ammonium-, tetraalkylammonium-, alkalimetal- or earth metal cation, to produce compounds of formula I.

7. Intermediates of formulae II, III, and IV as defined in claim 5.

8. A composition suitable for controlling phytopathogenic fungi, comprising a solid or liquid carrier and a compound of the formula I as claimed in claim 1.

9. A method for controlling phytopathogenic fungi, which comprises treating the fungi or the materials, plants, the soil or the seed to be protected against fungal attack with an effective amount of a compound of the formula I as claimed in claim 1.

* * * * *